United States Patent
Nozawa et al.

(10) Patent No.: US 6,462,051 B1
(45) Date of Patent: Oct. 8, 2002

(54) COMPOSITION FOR REDUCING MENTAL FATIGUE, COMPOSITION FOR MAINTAINING AND ENHANCING CONCENTRATION, AND COMPOSITION FOR MAINTAINING AND ENHANCING MENTAL VIGOR

(75) Inventors: Ayumu Nozawa; Yuko Sagesaka; Akio Sugimoto; Takami Kakuda, all of Shizuoka (JP)

(73) Assignee: Ito En, Ltd., Tokyo (JP)

(*) Notice: Subject to any disclaimer, the term of this patent is extended or adjusted under 35 U.S.C. 154(b) by 0 days.

(21) Appl. No.: 09/951,673

(22) Filed: Sep. 14, 2001

(30) Foreign Application Priority Data

Apr. 25, 2001 (JP) ........................................ 2001-128279

(51) Int. Cl.⁷ .............................................. A61R 31/52
(52) U.S. Cl. ........................................ 514/264; 514/263
(58) Field of Search .................................. 514/263, 264

(56) References Cited

U.S. PATENT DOCUMENTS 5,427,806 A * 6/1995 Ekanayake et al. ...... 426/330.3
5,736,575 A * 4/1998 Kakuda et al. ............. 514/563
5,910,308 A * 6/1999 D'Jang .................... 424/195.1
6,271,259 B1 * 8/2001 Kakuda et al. ............. 514/563
6,297,280 B1 * 10/2001 Ishihara et al. ............. 514/563

OTHER PUBLICATIONS

Shin, First International symposium on Green Tea., Sep. 22, 1989.*

* cited by examiner

Primary Examiner—James H Reamer
(74) Attorney, Agent, or Firm—Sughrue Mion, PLLC

(57) ABSTRACT

The present invention is intended to provide compositions which exert excellent effects allowing improvement in the mental function of humans and animals other than humans, such as reduction of mental fatigue, maintenance and enhancement of concentration maintenance and enhancement of mental vigor, and the like. These compositions are provided as mentally functional compositions containing, as the active component, a mixture component comprising caffeine, theanine, and arginine which are contained in tea. It is preferable that caffeine, theanine, and arginine are mixed such that the mixing ratio approaches a ratio of 1:2:2. Further, by combining the above-described mixture component with sugar and citric acid, mentally functional foods and beverages can be also provided which are taken with ease and effective.

12 Claims, 5 Drawing Sheets

COMPOSITION FOR REDUCING MENTAL FATIGUE, COMPOSITION FOR MAINTAINING AND ENHANCING CONCENTRATION, AND COMPOSITION FOR MAINTAINING AND ENHANCING MENTAL VIGOR

BACKGROUND OF THE INVENTION

1. Field of the Invention

The present invention relates to compositions which exert excellent effects allowing improvement in the mental function of humans and animals other than humans, such as reduction of mental fatigue which is caused by physical load, mental load, or other various factors, maintenance and enhancement of concentration, maintenance and enhancement of mental vigor, and the like.

2. Related Art Statement

It is said that classification of mental fatigue and physical fatigue is generally difficult. Certainly, when physical fatigue continues, one gradually comes to feel mental fatigue as well, and the power of concentration will fall off simultaneously. This is an experience that people undergo usually, and it is tree that the mental fatigue and the physical fatigue are closely associated with each other in many cases.

However, some mental fatigue may arise only from mental factors such as mental stress, mental disorder, and the like, and it is also said that the fatigue of the moderns is largely caused by this kind of mental fatigue rather than physical fatigue.

In some cases, symptoms characteristic of mental fatigue such as lack of concentration, emotional instability, sleep disturbance, and the like will appear. From the viewpoint of treatment and prevention, a sufficient rest can lead to a complete recovery from physical fatigue in many cases, but mental fatigue has characteristic properties that it is difficult to make a complete recovery only by means of taking a rest. On the other hand, for example, in the case where one waits for his/her game which is started several hours later or on the next day, such as at sport games or the like, if the mental function can be filed up by some way or other, then an effective influence on the game result can be expected, even though it is difficult to recover from physical fatigue in a short time.

Such problems related to the mental function have become serious even in animals other than humans, such as cats, dogs, horses, and others. For example, mental fatigue in a race horse will arise in the case where the mental power is used to an extent more than required, and it is said that unlike physical fatigue, it is difficult to bring about a recovery from mental fatigue even by taking a rest, and is 'hard to come out to the surface' of the horse. That is, such fatigue does not appear in its physical condition and is difficult to get to Snow by training, and even if a trainer has judged that 'the fatigue has been gone', it still remains actually, with the result that, for example, the horse is not extended at all in the last straightaway of a racecourse.

As mentioned above, problems from the mental function in humans and animals other than humans have an aspect entirely different from those from the physical function such as physical fatigue and the like. Therefore, if material(s) exerting a positive and effective action on the mental function can be found out, then such materials(s) can be used very effectively.

Conventionally, for example, materials such as honey of acacia, *Mallotus japonicus,* milk, *Panax ginseng* C. A. Meyer, and others, which are quite different from the active component of the present invention, are said to have an effect on reducing stress and mental fatigue, and used as folk medicines.

Further, Japanese Laid-open Patent Publication No. 126, 179/1995 discloses that foods containing maracuja juice as the active component has a α-wave enhancing effect and contributes to reducing stress.

SUMMARY OF THE INVENTION

In order to solve the above-mentioned problems, the inventors have extensively examined effects on the mental function of various components contained in tea. As a result, it has been found that maintenance and enhancement of the mental function can be promoted positively and effectively when caffeine, theanine, and arginine are used in combination. Thus, the inventors have reached the present invention on the basis of these findings.

That is, the present invention provides a composition for reducing mental fatigue, a composition for maintaining and enhancing concentration, and a composition for maintaining and enhancing mental vigor, as a mentally functional composition containing, as the active component, a mixture component comprising caffeine, theanine, and arginine.

Herein, the mentally functional composition means a composition which has biological and medical functions relating to the mental function such as mental fatigue, concentration, mental vigor, and the like of humans and animals other than humans. As used herein, the composition for reducing mental fatigue means a composition which possesses functions capable of reducing mental fatigue caused by various factors such as physical load, mental load, and the like; the composition for maintaining and enhancing concentration means a composition which has effects of controlling the fall in concentration caused likewise by various factors and of enhancing concentration; and the composition for maintaining and enhancing mental vigor means a composition which has effects of controlling the fall in mental vigor caused likewise by various factors and of enhancing mental vigor.

DETAILED DESCRIPTION

Figure 1:
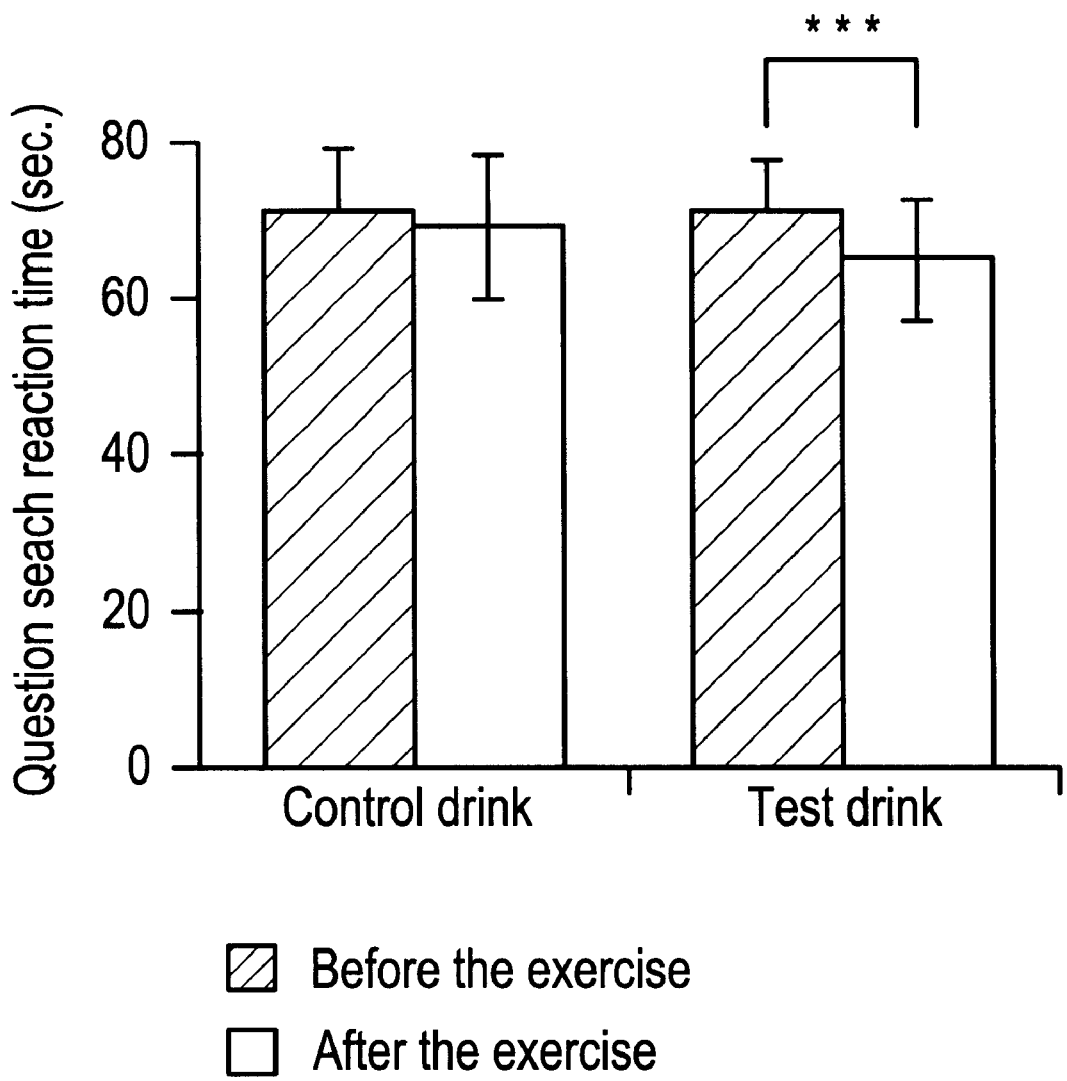
FIG. 1 is a graph showing the results obtained by measuring the reaction time in the ATMT question search when a test drink was given and when a control drink ('control') was given to evaluate the concentration power in Examination 1.

The mentally functional compositions of the present invention, including composition for reducing mental fatigue, composition for maintaining and Enhancing concentration, and composition for maintaining and enhancing mental vigor, can be prepared by containing, as the active component, a mixture component comprising caffeine, theanine, and arginine.

In the present invention, a mentally functional composition refers to the group including composition for reducing mental fatigue, composition for maintaining and enhancing concentration, and composition for maintaining and enhancing mental vigor.

In the present invention, it is preferable that caffeine, theanine, and arginine are mixed at such ratios that the ratio for the caffeine is less than 1:1:1, and in particular ratios approaching 1:2:2, at which ratios a particularly excellent effect on the mental functionality has been confirmed. However, the present invention should not be limited to this range.

A mixture component comprising caffeine, theanine, and arginine, as the active component in the invention, can be obtained not only by extraction from tea, but also by mixing the respective ingredients after obtaining them separately. These ingredients can be obtained by extraction from natural sources such as tea, coffee, and the like, by chemical synthesis, microbial fermentation or plant tissue culture, or by other producing methods.

Caffeine in the invention is intended to include anhydrous caffeine, and can be obtained by extraction from tea leaves or coffee beans, for example, with hot water, filtration, and evaporation to dryness, followed by re-extraction from the obtained dry residue, for example, with ethanol, or by synthesis with the Traube method or the like. Caffeine commercially available can be used for the invention as well.

As theanine in the invention can be used at least one member selected from the group consisting of L- or D-glutamic acid γ-alkylamide, such as L-glutamic acid γ-ethylamide (L-theanine), L-glutamic acid γ-methylamide, D-glutamic acid γ-ethylamide (D-theanine), and D-glutamic acid γ-methylamide, and derivatives having an L- or D-glutamic acid γ-alkylamide group as the basic structure (for example, glycosides of L- or D-glutamic acid γ-alkylamide and others). Among them, L-theanine is especially preferable from the viewpoint of availability and safety, because it not only can be obtained from natural sources but also is approved as a food additive.

Theanine can be obtained by various methods already known. Concretely, theanine can be obtained by biosynthesis using methods in which plants or microorganisms are cultured, by extraction from tea leaves, and also by fermentation or chemical synthesis.

As arginine in the invention may be used isomers and derivatives of its L-form compounds and the like, and its physiologically acceptable salts such as L-arginine hydrochloride and others. Arginine is contained at large amounts in milt, cuttlefish, garlic, and the like, and can be obtained by purification from these natural sources. In addition, L-arginine, L-arginine hydrochloride, L-arginine L-glutamate, and others which are commercially available can be used.

The mentally functional compositions of the present invention can be prepared by containing, as the active component, a three-ingredient mixture alone which is composed of caffeine, theanine, and arginine (preferably having a ratio of 1:2:2), or alternatively a mixed component formed by adding to the three-ingredient mixture one or more kinds of other materials for the mental function such as honey of acacia, *Mallotus japonicus*, milk, *Panax ginseng* C. A. Meyer, and the like which have been utilized traditionally as folk medicines for reducing mental stress.

In the compositions of the present invention, the amount of the above-mentioned three-ingredient mixture to be mixed is not limited in particular. However, on the basis of fatigue examinations which the inventors were carried out using rats, described in Japanese Patent Laid-open Publication No. 187 736/2001 (Japanese Patent Application No. 35,345/2000), it has been found that administration at 50 mg/kg-weight or higher resulted in increasing the level of catecholamine in blood too high, so that excessive exercise was caused, and the production of ketone bodies which are produced due to fatigue cannot be controlled, and thus may conversely accumulate fatigue. Taking this point into consideration, it is preferable that the compositions are prepared such that the single dosage of the active component of the invention is not more than 50 mg/kg-weight. For example, supposing the body weight is 30 to 80 kg, the content of the active component in the mentally functional foods or beverages is preferably adjusted at about 15 to 4,000 mg. In the case where the compositions are provided as forms allowing taking at a time, for example, two or three tablets, candies, or the like, the content may be adjusted at about 3 to 500 mg per piece.

The mentally functional compositions of the present invention can be used for various applications such as medicines, quasi drugs, health foods and beverages, food additives, feeds, feed additives, and the like. As forms in such applications, the compositions can be provided as dry powders by freeze drying, spray drying, or the like, and as solutions, tablets, powders, granules, dragees, capsules, suspensions, emulsions, ampules, injections, and any other suitable form.

In the case of providing the compositions as a medicine, for example, the compositions may be prepared by dissolving the active component directly in purified water, a physiological saline solution, or the like. Further, the compositions may be produced as a quasi drug, which in turn is formed into forms for drinking, such as bottled drinks, or into forms such as tablets, capsules, or granules, and then into various forms such as health foods and beverages, food additives, feeds, and feed additives, by adding materials usually combined to produce respective foods or beverages capable of being provided as agents for preventing the fall in the mental function which can be taken as easily as possible. For example, to the active component in the invention can be added one or more materials selected from food materials including fruits, jerry, or the like, milk components, carbonic acid, vehicles including pelletizing agents, diluents, and additionally, sweetenings, flavors, glucides such as flour, starches, sugars, and the like, various proteins, oils and fats, physiologically active ingredients such as vitamins, minerals, and the like, hormones, nourishing components, and the like, whereby the compositions of the present invention can be provided as a variety of forms of foods and beverages, for example, beverages such as sport drinks, fruit beverages, tea beverages, vegetable juices, dairy beverages, milk beverages, alcoholic drinks, jelly drinks, carbonated drinks, and the like; confectionaries such as jelly, chewing gum, chocolate, ice cream, candy, biscuit, or the like; starch-based processed foods such as snacks, breads, cakes, or the like; protein-based processed foods such as fish meat paste products, livestock meat products, soybean curd, cheese, or the like; seasoning such as miso (soybean paste), soy sauce, dressing, or the like; and supplements, feeds, pet foods or the like.

In particular, the composition for reducing mental fatigue, the composition for maintaining and enhancing concentration, and the composition for maintaining and enhancing mental vigor are prepared by combining the mixture component comprising caffeine, theanine, and arginine with sugar and citric acid, and based on these compositions, the above-mentioned medicines, quasi drugs, health foods and beverages, food additives, feeds, feed additives or the like are produced, so that useful products which are able to be easily taken can be provided.

The compositions of the present invention can promote controlling the fall in and enhancing the mental function by taking them after one actually feels the fall in the mental function, such as mental fatigue, the fall in concentration, the fall in mental vigor, or other, and as well preventing the fall in the mental function by taking them in advance.

Moreover, the compositions of the present invention can be taken in safety by humans, as well as animals other than humans, and are extremely suitable for daily taking, because the active component of the compositions of the present intention is composed of tea extracted ingredients which have been taken daily from the ancient times.

In the present invention, animals other than humans encompass mammals such as dogs, cats, horses, and cattle, birds such as domestic fowl, and all other animals which can feel mental stress.

Most of the conventional compositions claimed to have a nourishing and tonic effect have been developed putting the principal object to the physical function such as physical fatigue and the like, and thus maintenance and enhancement of the mental function, such as recovery from mental fatigue and the like, are presumed only as a subsidiary or secondary effect. For this reason, there have been found few conventional compositions whose effect is actually confirmed on the mental function.

For example, Japanese Patent Laid-open Publication No. 143,377/1991 (Japanese Patent Application No. 278,479/1989) discloses that caffeine as an extracted component of tea contributes to the continuation of stamina during the exercise, and at the same time, in the third example that either a beverage consisting of caffeine and water or an extracted liquid of natural oolong tea containing the same amount of caffeine was given for twenty consecutive days to compare the stamina continuation, so that a better effect on the stamina continuation can be obtained by taking the extracted liquid of natural oolong tea. However, no examination was carried out as to mental fatigue or mental vigor.

In addition, Japanese Patent Laid-open Publication No. 330,593/1995 discloses fatigue-relieving agents containing ubiquinone and biotin as active ingredients which have an effect on promoting recovery from physical and mental fatigue and the like. It develops an argument that these agents have an effect of facilitating the ATP production, so that they are effective for promoting recovery from physical and mental fatigue. However, no examination was carried out as to recovery from mental fatigue.

EXAMINATION 1

Hereinafter, the inventors investigated the influence of the mixture component comprising caffeine, theanine, and arginine, on the mental function, in particular. an influence on mental fatigue tiredness, concentration, and mental vigor.

A test drink was prepared by mixing 30 mg of caffeine, 60 mg of theanine, and 60 mg of arginine, and adding 10% liquid sugar of fructose and glucose and 1% citric acid to obtain a 190 mL test drink.

On the other hand, as a control drink, a solution containing 0.03% of Acesulfame K (a sweetening), 0.07% of tartaric acid and an appropriate amount of flavors was prepared.

Acesulfame K is a water-soluble sweetening having a sweetness of 200 times sucrose and a high solubility, and is resistant to acid, heat, and oxidation.

Tartaric acid is a carboxylic acid contained in grape and the like, and is often used as an additive for beverages containing grape juice and the like. Tartaric acid is very soluble in water, and known medically and biochemically to be hardly absorbed by oral administration. This acid is also used as a mild refreshing and anti-thirst agent and is inactive in the body of animals.

Twenty four healthy persons aged between 19 and 48 years were selected as subjects. A set of two examinations in which each subject was given a control drink (a control examination) and a test drink (an examination receiving a test drink).

The subjects were given the test drink or the control drink at the time of 30 minutes before starting an exercise, and a 40-minute running was imposed on subjects aged less than 80 years old, a 40-minute jogging on subjects aged not less than 30 and less than 40 years old, and a 40-minute jogging and walk on subjects aged not less than 40 years old. Before and after the exercise, the subjects were measured for each of the concentration power, the fatigue tiredness, and the degree of fatigue and vigor.

That is, Examination 1 was carried out according to the following protocol: the subjects were subjected to measuring fatigue tiredness, taking a drink, taking a rest for 30 minutes, imposing the exercise for 40 minutes, and measuring the fatigue tiredness and others.

For the concentration power, the reaction time in the ATMT question search was measured as an index, and the results are shown in FIG. 1.

The ATMT question is a task in which a monitor (person under testing) is required to push randomly-arranged figures in order as fast as possible, and is known to have a strong correlation with the degree of mental fatigue, the degree of awakening, and others.

Figure 2:
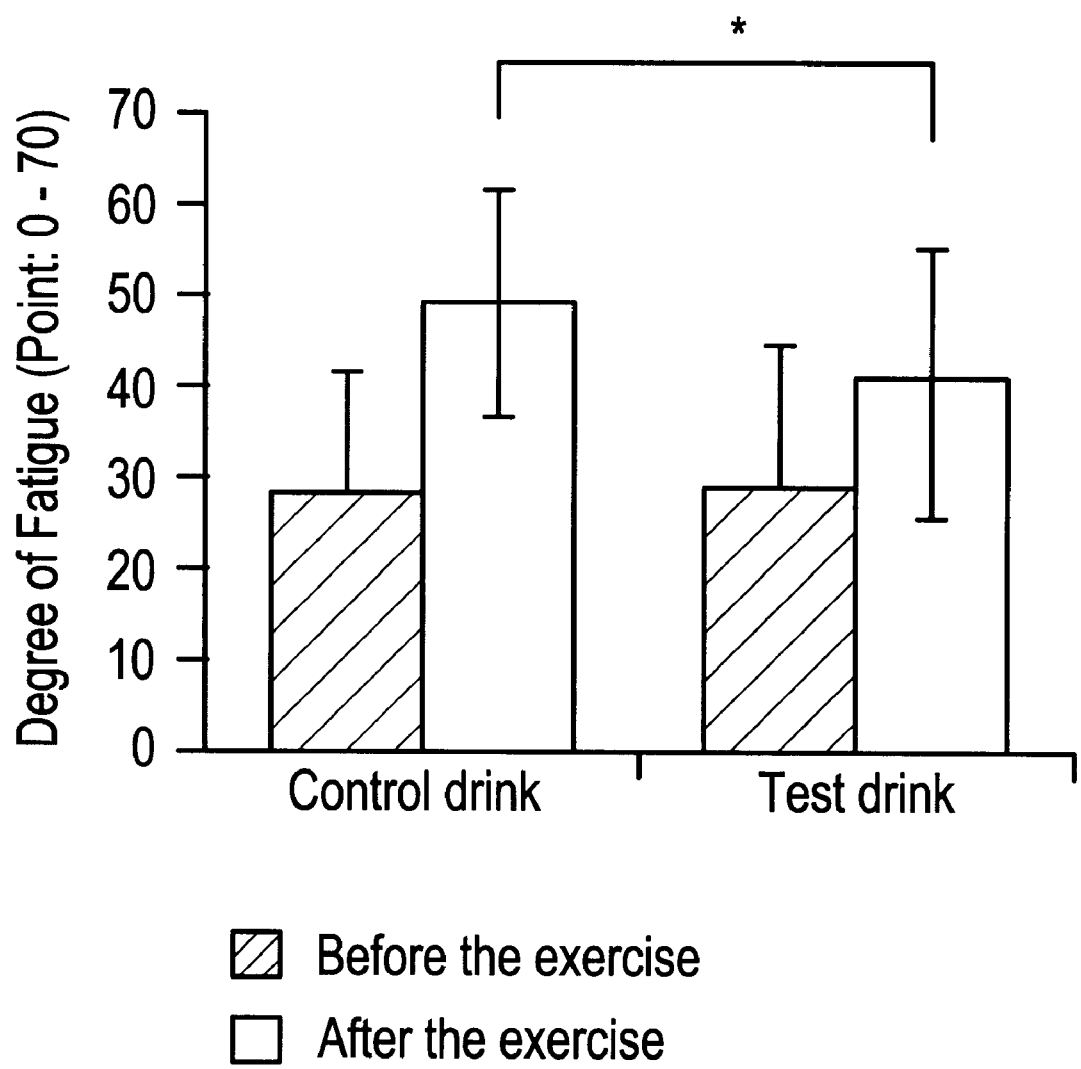
FIG. 2 is a graph showing the results obtained by estimation using the self-rating scale for mental fatigue ('VAS') when a test drink was given and when a control drink ('control') was given to evaluate the fatigue tiredness in Examination 1.

For the estimation of the mental fatigue tiredness, measurements were made using the self-rating scale for mental fatigue ('VAS'), and the results are shown in FIG. 2.

The estimation of mental fatigue tiredness by VAS is based on a method in which the degree of mental fatigue tiredness at a given time is plotted by the subjects under testing on the line segment from 0 (not tired) to 70 (extremely tired).

Figure 3:
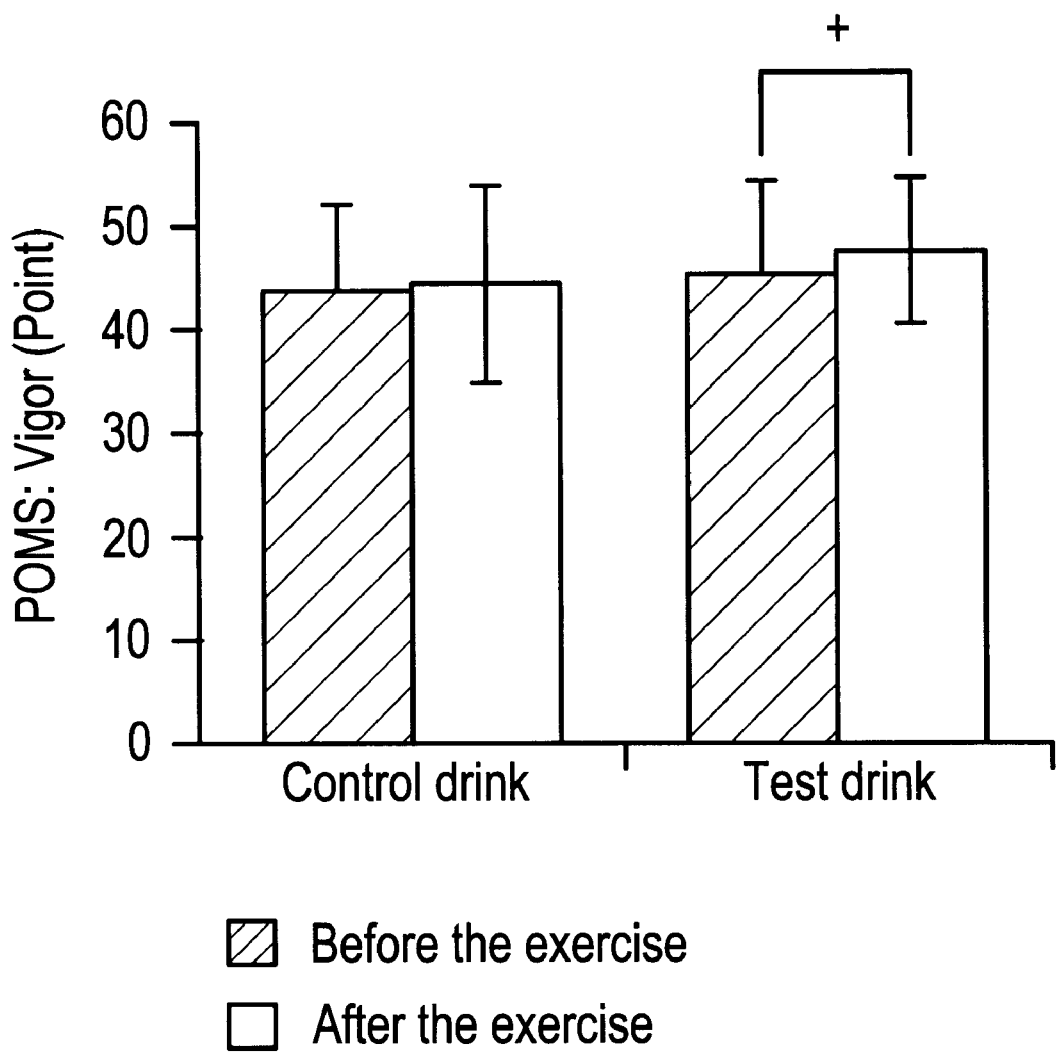
FIG. 3 is a graph showing the results obtained by measuring 'vigor' scores using the POMS (profiled of mood state) feeling rating scale when a test drink was given and when a control drink ('control') was given to evaluate the degree of mental vigor in Examination 1.
Figure 4:
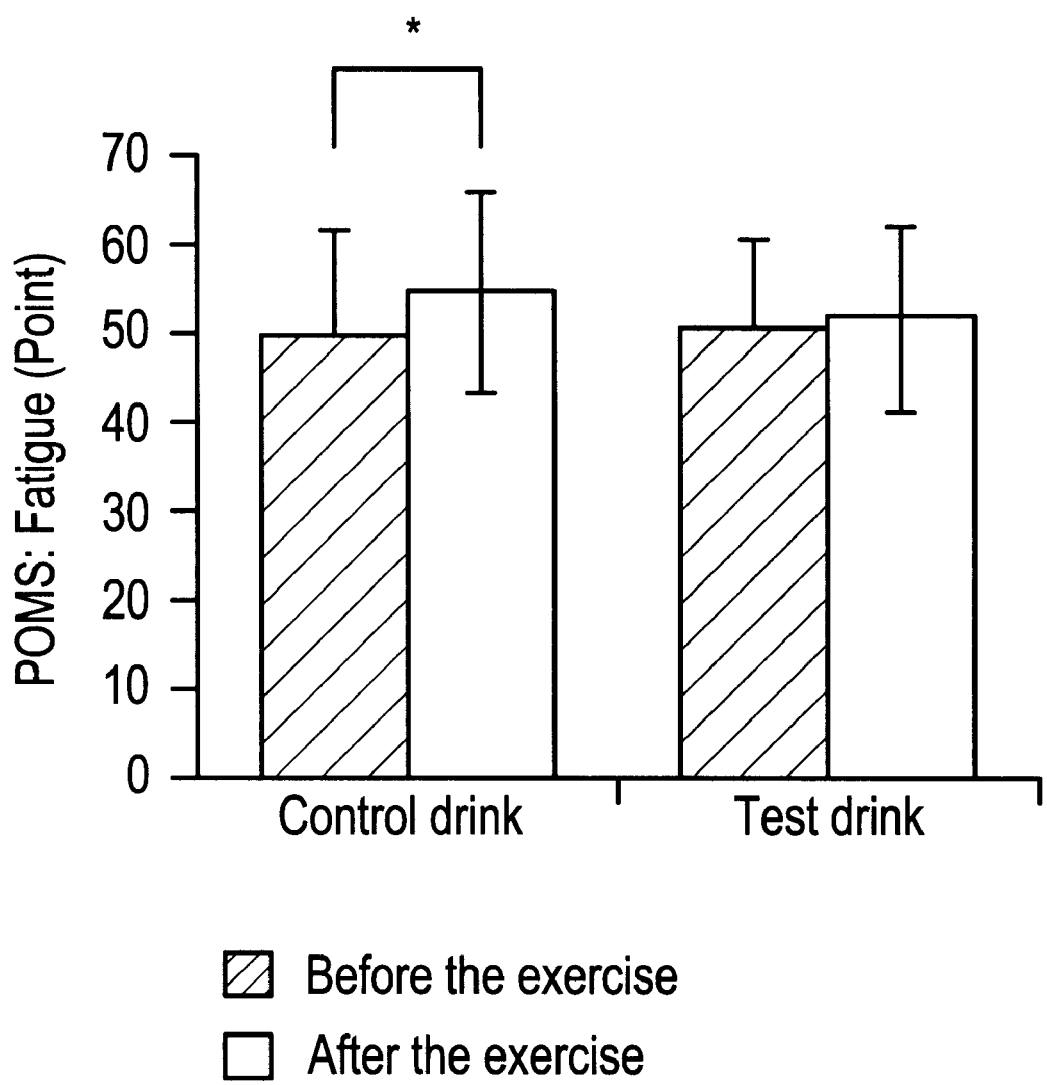
FIG. 4 is a graph showing the results obtained by measuring 'fatigue' scores using the POMS feeling rating scale when a test drink was given and when a control drink ('control') was given to evaluate the degree of mental fatigue in Examination 1.

The degree of mental fatigue and the degree of mental vigor were estimated using the POMS feeling rating scale, and the results are shown in FIGS. 3 and 4 for the degree of mental vigor and the degree of mental fatigue, respectively The POMS feeling-rating scale is one of questionary paper methods in which a feeling at a given time is objectively estimated using a questionary paper, and is a rating scale which is internationally most authorized.

(RESULTS)

Comparing the reaction time before and after the exercise in FIG. 1, in the examination receiving the test drink, the reaction time was shortened significantly after the exercise, relative to before the exercise, which shows that the test drink has an effect of elevating and maintaining the concentration power, and the quickness and flexibility of mind.

Comparing the degree of increasing mental fatigue by loading the exercise in FIG. 2, it can be understood that the examination receiving the test drink shows a significantly lower degree of increasing mental fatigue It is likely that the test drink will reduce the mental fatigue tiredness caused by loading an exercise.

Comparing the degree of mental fatigue and the degree of mental vigor in FIGS. 3 and 4, the 'vigor' scores were increased and the 'fatigue' scores did not change in the examination receiving the test drink, although the 'vigor' scores did not change and the 'fatigue' scores were increased after the exercise in the control examination. This shows that the test drink enhances an active feeling, as well as that it reduces the mental fatigue tiredness caused by loading an exercise.

Summarizing the above, by taking the test drink, the reaction time after the exercise can be significantly shortened in the ATMT question search test, and the rate of increasing mental fatigue is significantly lowered in the VAS score, compared to the control examination. Furthermore, in the POMS feeling rating scores, the increase in the 'fatigue' score is controlled and the increase in the 'vigor' score will be recognized.

That is, it has been found that the mental fatigue tiredness can be reduced by taking the test drink, and additionally, an effect of elevating and maintaining the concentration power and mental vigor can be obtained instead, even afterc fatigue is given.

EXAMINATION 2

Eight healthy males aged between 20 to 29 years were selected as subjects. A set of two examinations in which each subject was given a control drink (a control examination) and a test drink (an examination receiving a test drink) was carried out.

Figure 5:
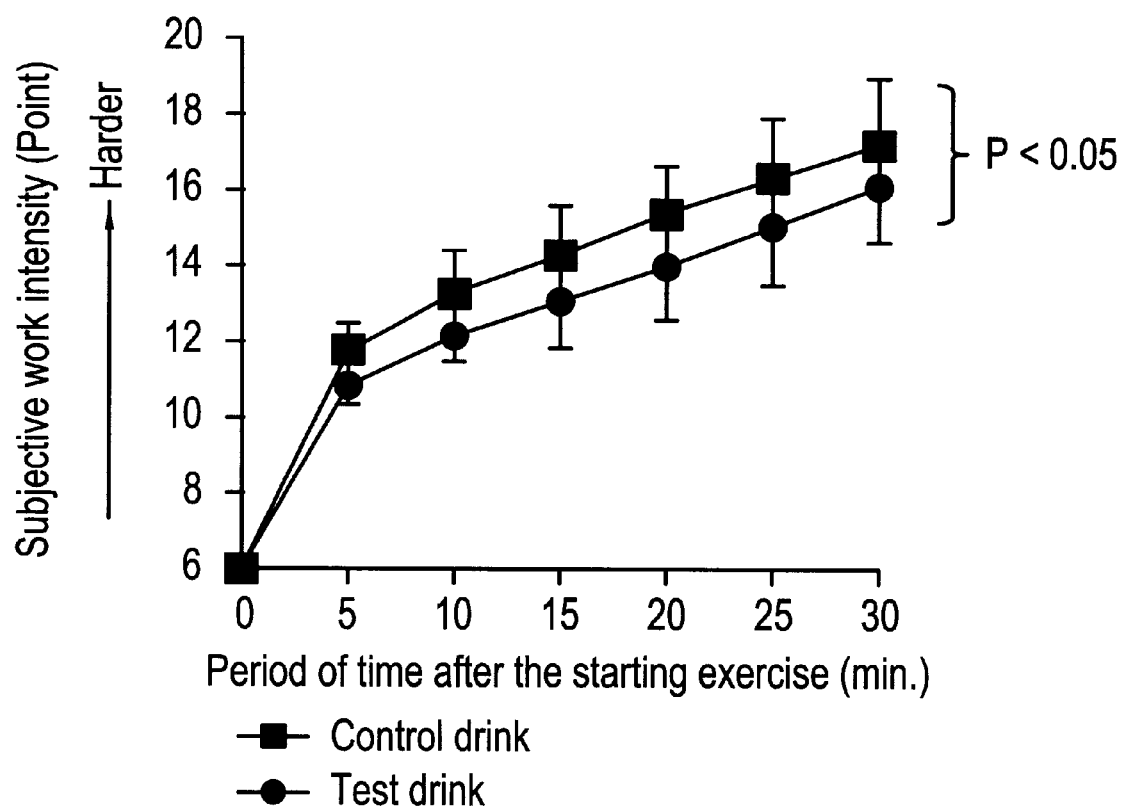
FIG. 5 is a graph showing the comparison of the subjective intensity of mental fatigue during the exercise when a test drink was given and when a control drink ('control') was given in Examination 2.

In these examinations, the subjects were given the same test drink as in Examination 1 or the same control drink as in Examination 1 at the time of 30 minutes before starting an exercise. Then, a treadmill running (a jogging using a treadmill like a Room-runner) corresponding to a $VO_2$max of 75% was imposed in conditions of a room temperature of 21° C., a humidity of 50%, and a gradient of 3° During the running, the subjective fatigue intensity was judged by the subjects at intervals of five minutes after starting the exercise, and the results are shown in FIG. 5.

That is, Examination 2 was carried out according to the following protocol: the subjects were subjected to taking a rest for one hour, taking a drink, taking a rest for 30 minutes, and running on a treadmill for 30 minutes.

The subjective fatigue intensity was set from 6 points during the rest to 20 points at the maximum, and the work intensity (hardness of working and mental fatigue tiredness) at the respective times was determined by the subjects using such a rating system.

The treadmill running corresponding to a $VO_2$max of 75% has an intensity of exercise corresponding to 75% of the maximum heart rate, and is equivalent to an average speed of about 7 to 11 km/h for the subjects in these examinations.

As can be seen from the results in FIG. 5, it has been understood that the mental fatigue tiredness in the examination receiving the test drink is significantly lower during the period from 5 minutes after starting the exercise to the end.

DESCRIPTION OF PREFERRED EMBODIMENTS

EXAMPLE 1

A preparation for reducing mental fatigue, maintaining and enhancing concentration, and maintaining and enhancing mental vigor was prepared by the following formulation:

In 10 g of total amount:

| | |
|---|---|
| L-arginine: | 50 mg |
| L-theanine: | 50 mg |
| Caffeine: | 50 mg |
| Vitamin C: | 1000 mg |
| Vitamin $B_1$: | 1 mg |
| Vitamin $B_2$: | 1 mg |
| Vitamin $B_6$: | 1 mg |
| Pelletizing agent: | as appropriate |
| Flavor: | as appropriate |

EXAMPLE 2

A functional beverage for reducing mental fatigue, maintaining and enhancing concentration, and maintaining and enhancing mental vigor was prepared by the following formulation:

| | |
|---|---|
| Fruit juice: | 1 wt % |
| Liquid sugar of fructose and glucose: | 40 wt % |
| Citric acid: | 1 wt % |
| Vitamin C: | 1 wt % |
| Vitamin $B_1$: | 0.1 wt % |
| Vitamin $B_2$: | 0.1 wt % |
| Vitamin $B_6$: | 0.1 wt % |
| L-arginine: | 3 wt % |
| L-theanine: | 3 wt % |
| Caffeine: | 3 wt % |
| Flavor: | 0.1 wt % |
| Water: | balance |

What is claimed is:

1. A composition for reducing mental fatigue containing, as active component, a mixture component comprising caffeine, theanine, and arginine, characterized in that the mixing ratio of caffeine, theanine, and arginine is such that the ratio for the caffeine is less than 1:1:1.

2. A composition for reducing mental fatigue containing, as active component, a mixture component comprising caffeine, theanine, and arginine, characterized in that the mixing ratio of caffeine, theanine, and arginine is 1:2:2.

3. A composition according to claim 2, wherein the composition contains, as the active component, a mixed component in which sugar and citric acid are added to said mixture component comprising caffeine, theanine, and arginine.

4. A composition according to claim 1, wherein the composition contains, as the active component, a mixed component in which sugar and citric acid are added to said mixture component comprising caffeine, theanine, and arginine.

5. A composition for maintaining and enhancing concentration containing, as active component, a mixture component comprising caffeine, theanine, and arginine characterized in that the mixing ratio of caffeine, theanine and arginine is such that the ratio for the caffeine is less than 1:1:1.

6. A composition for maintaining and enhancing concentration containing, as active component, a mixture component comprising caffeine, theanine, and arginine, characterized in that the mixing ratio of caffeine, theanine, and arginine is 1:2:2.

7. A composition according to claim 6, wherein the composition contains, as the active component, a mixed component in which sugar and citric acid are added to said mixture component comprising caffeine, theanine, and arginine.

8. A composition according to claim 5, wherein the composition contains, as the active component, a mixed component in which sugar and citric acid are added to said mixture component comprising caffeine, theanine, and arginine.

9. A composition for maintaining and enhancing mental vigor containing, as active component, a mixture component comprising caffeine, theanine, and arginine, characterized in that the mixing ratio of caffeine, theanine, and arginine is such that the ratio for the caffeine is less than 1:1:1.

10. A composition for maintaining and enhancing mental vigor containing, as active component, a mixture component comprising caffeine, theanine, and arginine, wherein characterized in that the mixing ratio of caffeine, theanine and arginine is 1:2:2.

11. A composition according to claim 10 wherein the composition contains, as the active component, a mixed component in which sugar and citric acid are added to said mixture component comprising caffeine, theanine, and arginine.

12. A composition according to claim 9, wherein the composition contains, as the active component, a mixed component in which sugar and citric acid are added to said mixture component comprising caffeine, theanine, and arginine.

* * * * *